(12) United States Patent
Chen et al.

(10) Patent No.: US 9,023,644 B2
(45) Date of Patent: May 5, 2015

(54) FGF HAVING ENHANCED STABILITY

(71) Applicant: Wisconsin Alumni Research Foundation, Madison, WI (US)

(72) Inventors: Guokai Chen, Rockville, MD (US); James A. Thomson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/717,055

(22) Filed: Dec. 17, 2012

(65) Prior Publication Data

US 2013/0157359 A1    Jun. 20, 2013

Related U.S. Application Data

(60) Provisional application No. 61/576,803, filed on Dec. 16, 2011.

(51) Int. Cl.
*C12N 5/00*      (2006.01)
*C12N 5/0735*    (2010.01)
*C12N 5/074*     (2010.01)

(52) U.S. Cl.
CPC ............ *C12N 5/0606* (2013.01); *C12N 5/0696* (2013.01); *C12N 2501/113* (2013.01); *C12N 2501/91* (2013.01); *C12N 2506/02* (2013.01); *C12N 2506/1307* (2013.01)

(58) Field of Classification Search
USPC .................................................. 435/325, 377
See application file for complete search history.

(56) References Cited

U.S. PATENT DOCUMENTS

| | | | |
|---|---|---|---|
| 6,692,961 B1 | 2/2004 | Judd | |
| 7,659,379 B1 | 2/2010 | Blaber | |
| 2010/0221829 A1* | 9/2010 | Amit et al. | 435/366 |

OTHER PUBLICATIONS

Humphrey et al. Stem Cells 22:522-530, 2004.*
Tamizawa et al. Journal of Cellular Biochemistry 114:584-588, 2013.*
Beattie et al. Stem Cells 23:489-495, 2005.*
Eiselleova et al (2009), "A complex role for FGF-2 in self-renewal, survival, and adhesion of human embryonic stem cells," Stem Cells; Aug;27(8):1847-1857.
Lanner et al (2010), "The role of FGF/Erk signaling in pluripotent cells," Development, Oct;137(20):3351-3360.
Levenstein et al (2010), "Basic fibroblast growth factor support of human embryonic stem cell self-renewal," Stem Cells, Mar;24(3):568-574.
Vallier et al (2005), "Activin/Nodal and FGF pathways cooperate to maintain pluripotency of human embryonic stem cells," J Cell Sci., Oct. 1;118(Pt 19):4495-4509.
Xu, R.H. et al (2005), "Basic FGF and suppression of BMP signaling sustain undifferentiated proliferation of human ES cells," Nature Methods, Mar;2(3):185-190.
Ornitz et al (2001), "Fibroblast growth factors," (3):REVIEWS3005. Epub Mar. 9, 2001.
Itoh et al (2004), "Evolution of the Fgf and Fgfr gene families," Trends Genet, Nov;20(11):563-569.
Eswarakumar et al (2005), "Cellular signaling by fibroblast growth factor receptors," Cytokine Growth Factor Rev. Apr;16(2):139-149. Epub Feb. 1.
Chen et al., "Actin-Myosin Contractility Is Responsible for the Reduced Viability of Dissociated Human Embryonic Stem Cells", 2010, Cell Stem Cell, vol. 7, No. 2, pp. 240-248.
Zhang et al (2006), "Receptor specificity of the fibroblast growh factor family. The complete mammalian FGF family," J Biol Chem, Jun. 9;281(23):15694-15700. Epub Apr. 4, 2006.
Beenken et al (2009), "The FGF family: biology, pathophysiology and therapy," Nat Rev Drug Discov, Mar;8(3):235-53. doi: 10.1038/nrd2792.
Mohammadi et al (2005), "A protein canyon in the FGF-FGF receptor dimer selects from an à la carte menu of heparan sulfate motifs," Curr Opin Struct Biol, Oct;15(5):505-516.
Furue et al (2008), "Heparin promotes the growth of human embryonic stem cells in a defined serum-free medium," Proc Natl Acad Sci U S A., Sep. 9;105(36):13409-14. doi: 10.1073/pnas.0806136105. Epub Aug 25, 2008.
Levenstein et al (2008), "Secreted proteoglycans directly mediate human embryonic stem cell-basic fibroblast growth factor 2 interactions critical for proliferation," Stem Cells, Dec;26(12):3099-3107. Epub Sep. 18, 2008.
Zakrzewska et al (2009), "Increased protein stability of FGF1 can compensate for its reduced affinity for heparin," J Biol Chem., Sep. 11;284(37):25388-403. doi: 10.1074/jbc M109.001289. Epub Jul. 2, 2009.
Ludwig, T.E. et al., "Derivation of human embryonic stem cells in defined conditions", 2006, Nat. Biotechnol., vol. 24, pp. 185-187.
Amit, M. e al., "Feeder layer- and serum-free culture of human embryonic stem cells", 2004, Biol. Reproduction, vol. 70, pp. 837-845.
Bendall, S.C. et al., "IGF and FGF cooperatively establish the regulatory stem cell niche of pluripotent human cells in vitro", 2007, Nature, vol. 448, No. 7157, pp. 1015-1021.
Sato et al., "Maintenance of pluripotency in human and mouse embryonic stem cells through activation of Wnt signaling by a pharmacological GSK-3-specific inhibitor", 2004, Nat. Med., vol. 10, No. 1, pp. 55-63.
Wang, L. et al., "Self-renewal of human embryonic stem cells requires insulin-like growth factor-1 receptor and ERBB2 receptor signaling", 2007, Blood, vol. 110, No. 12, pp. 4111-4119.
Ludwig, T.E. et al., "Feeder-independent culture of human embryonic stem cells", 2006, Nature Methods, vol. 3, pp. 637-646.
Chen, G. et al., "Chemically defined conditions for human iPS cell derivation and culture", Nat. Methods, 2011, vol. 8, No. 5, pp. 424-429.

(Continued)

*Primary Examiner* — Marcia S Noble
(74) *Attorney, Agent, or Firm* — Quarles & Brady LLP

(57) ABSTRACT

Methods are provided that exploit thermostable FGF-1 proteins for support of human pluripotent stem cell cultures. Also provided are compositions containing thermostable FGF-1 for culturing of human pluripotent stem cells.

23 Claims, 13 Drawing Sheets

(56) References Cited

OTHER PUBLICATIONS

Zakrzewska, M. et al., "Highly Stable Mutants of Human Fibroblast Growth Factor-1 Exhibit Prolonged Biological Action", 2005, J. Mol. Biol., vol. 352, No. 4, pp. 860-875.

Zakrzeska, M. et al., "Design of fully active FGF-1 variants with increased stability", 2004, Protein Eng. Des. Sel., vol. 17, No. 8, pp. 603-611.

Kim, J. et al., "Identification of a Key Structural Element for Protein Folding Within β-Hairpin Turns", 2003, J. Mol. Biol., vol. 328, No. 4, pp. 951-961.

Byrch, S.R. et al., "Symmetric, Primary and Tertiary Structure Mutations within a Symmetric Superfold: A Solution, not a Constraint, to Achieve a Foldable Polypeptide", 2004, J. Mol. Biol., vol. 344, No. 3, pp. 769-780.

Lee, J. et al., "The Interaction between Thermodynamic Stability and Buried Free Cysteines in Regulating the Functional Half-Life of Fibroblast Growth Factor-1", 2009, J. Mol. Biol., vol. 393, No. 1, pp. 113-127.

Gimenez-Gallego, G. et al., "The complete amino acid sequence of human brain-derived acidic fibroblast growth factor", 1986, Biochem. Biophys. Res. Comm., vol. 138, No. 2, pp. 611-617 (1986).

Wiedlocha et al., "Stimulation of Proliferation of a Human Osteosarcoma Cell Line by Exogenous Acidic Fibroblast Growth Factor Requires both Activation of Receptor Tyrosine Kinase and Growth Factor Internalization", 1996, Mol. Cell. Biol., vol. 16, No. 1, pp. 270-280.

Chen et al., "Thermal stability of fibroblast growth factor protein is a determinant factor in regulating self-renewal, Differentiation, and reprogramming in human pluripotent stem cells", 2012, Stem Cells, vol. 30, No. 4, pp. 623-630.

\* cited by examiner

FIG. 2A-C
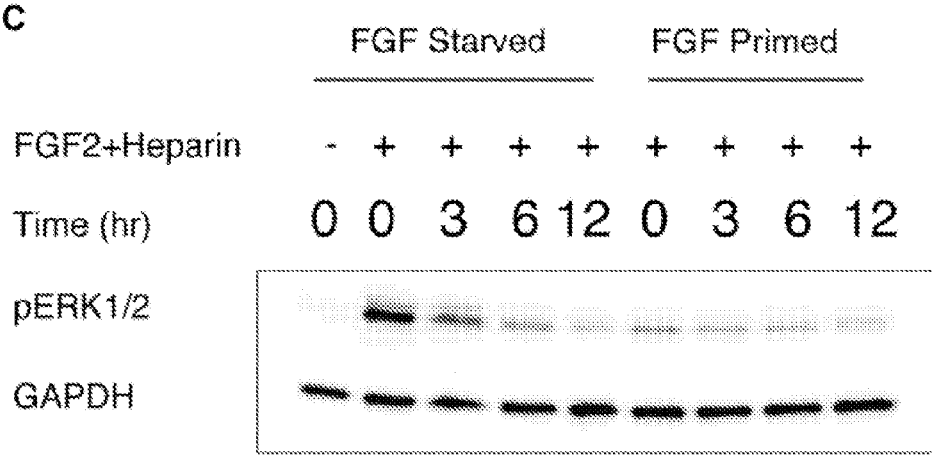

FIG. 3A-D
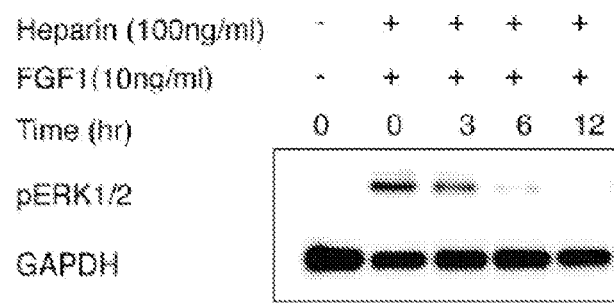
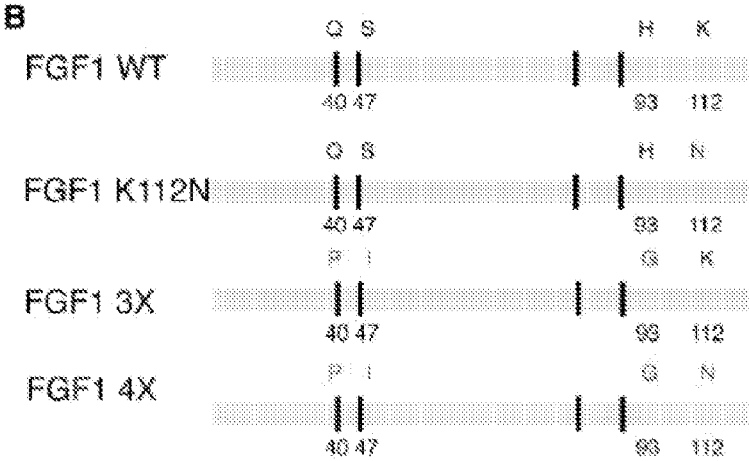

FIG. 3E AND 3F
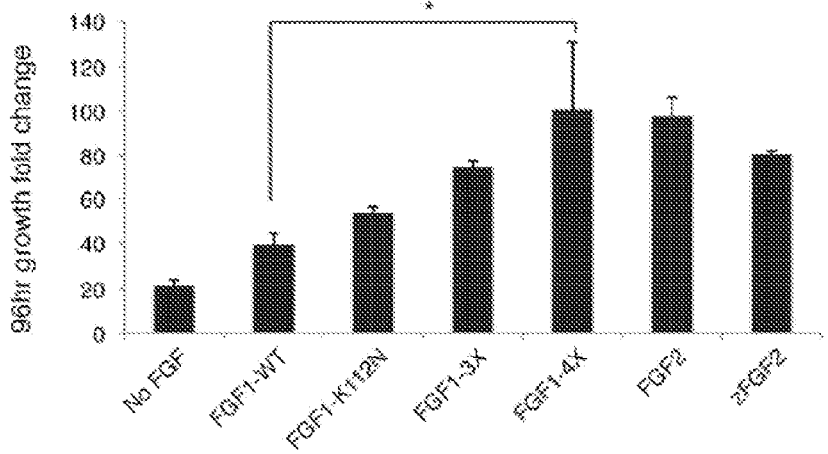
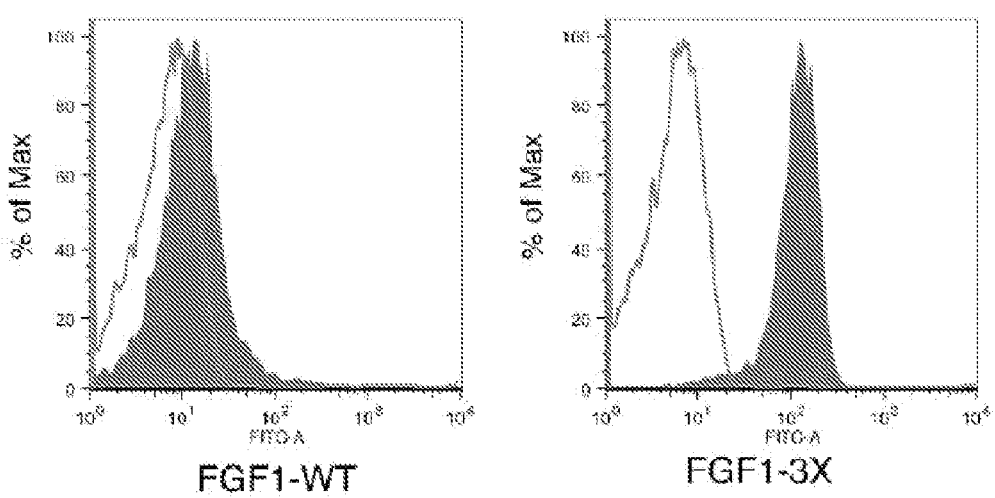
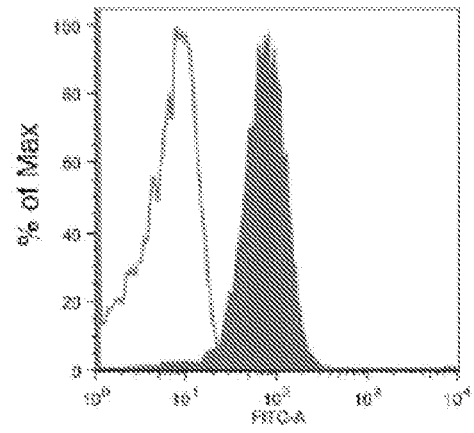

FIG. 4A-C
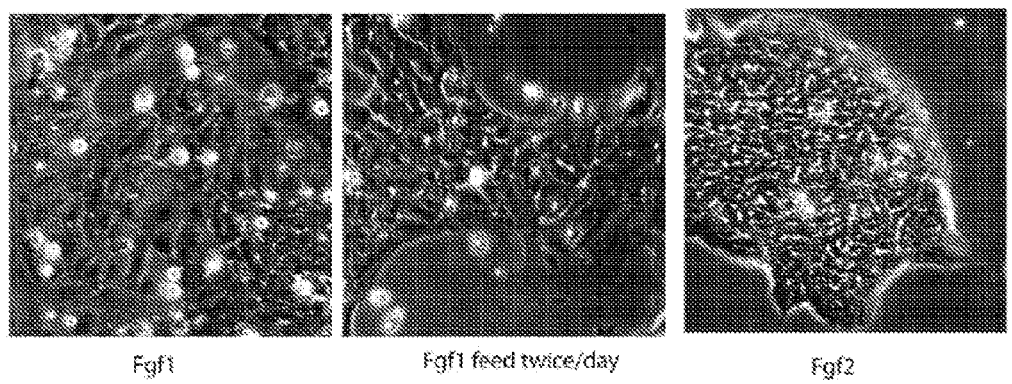

SEQUENCE LISTING

```
<160> NUMBER OF SEQ ID NOS: 4

<210> SEQ ID NO 1
<211> LENGTH: 411
<212> TYPE: DNA
<213> ORGANISM: Artificial Sequence
<220> FEATURE:
<223> OTHER INFORMATION: truncated wild type human FGF-1

<400> SEQUENCE: 1
atggctaatt acaagaagcc caaactcctc tactgtagca acgggggcca cttcctgagg      60
atccttccgg atggcacagt ggatgggaca agggacagga gcgaccagca cattcagctg     120
cagctcagtg cggaaagcgt gggggaggtg tatataaaga gtaccgagac tggccagtac     180
ttggccatgg acaccgacgg gcttttatac ggctcacaga caccaaatga ggaatgtttg     240
ttcctggaaa ggctggagga gaaccattac aacacctata tatccaagaa gcatgcagag     300
aagaattggt tgttggcct caagaagaat gggagctgca acgcggtcc tcggactcac      360 tatggccaga aagcaatctt gtttctcccc ctgccagtct cttctgatta a              411

<210> SEQ ID NO 2
<211> LENGTH: 136
<212> TYPE: PRT
<213> ORGANISM: Artificial Sequence
<220> FEATURE:
<223> OTHER INFORMATION: amino acid sequence of truncated wild type
      human FGF-1

<400> SEQUENCE: 2

Met Ala Asn Tyr Lys Lys Pro Lys Leu Leu Tyr Cys Ser Asn Gly Gly
1               5                   10                  15

His Phe Leu Arg Ile Leu Pro Asp Gly Thr Val Asp Gly Thr Arg Asp
            20                  25                  30

Arg Ser Asp Gln His Ile Gln Leu Gln Leu Ser Ala Glu Ser Val Gly
        35                  40                  45

Glu Val Tyr Ile Lys Ser Thr Glu Thr Gly Gln Tyr Leu Ala Met Asp
    50                  55                  60

Thr Asp Gly Leu Leu Tyr Gly Ser Gln Thr Pro Asn Glu Glu Cys Leu
65                  70                  75                  80

Phe Leu Glu Arg Leu Glu Glu Asn His Tyr Asn Thr Tyr Ile Ser Lys
                85                  90                  95

Lys His Ala Glu Lys Asn Trp Phe Val Gly Leu Lys Lys Asn Gly Ser
            100                 105                 110

Cys Lys Arg Gly Pro Arg Thr His Tyr Gly Gln Lys Ala Ile Leu Phe
        115                 120                 125

Leu Pro Leu Pro Val Ser Ser Asp
    130                 135

<210> SEQ ID NO 3
<211> LENGTH: 136
<212> TYPE: PRT
<213> ORGANISM: Artificial Sequence
```

```
<220> FEATURE:
<223> OTHER INFORMATION: truncated wild type human FGF-1 with Q40P,
      S47I, and H93G substitutions

<400> SEQUENCE: 3

Met Ala Asn Tyr Lys Lys Pro Lys Leu Leu Tyr Cys Ser Asn Gly Gly
1               5                   10                  15

His Phe Leu Arg Ile Leu Pro Asp Gly Thr Val Asp Gly Thr Arg Asp
                20                  25                  30

Arg Ser Asp Pro His Ile Gln Leu Gln Leu Ile Ala Glu Ser Val Gly
            35                  40                  45

Glu Val Tyr Ile Lys Ser Thr Glu Thr Gly Gln Tyr Leu Ala Met Asp
        50                  55                  60

Thr Asp Gly Leu Leu Tyr Gly Ser Gln Thr Pro Asn Glu Glu Cys Leu
65                  70                  75                  80

Phe Leu Glu Arg Leu Glu Glu Asn Gly Tyr Asn Thr Tyr Ile Ser Lys
                85                  90                  95

Lys His Ala Glu Lys Asn Trp Phe Val Gly Leu Lys Lys Asn Gly Ser
                100                 105                 110

Cys Lys Arg Gly Pro Arg Thr His Tyr Gly Gln Lys Ala Ile Leu Phe
            115                 120                 125

Leu Pro Leu Pro Val Ser Ser Asp
        130                 135

<210> SEQ ID NO 4
<211> LENGTH: 136
<212> TYPE: PRT
<213> ORGANISM: Artificial Sequence
<220> FEATURE:
<223> OTHER INFORMATION: truncated wild type human FGF-1 with Q40P,
      S47I, H93G, and K112N substitutions

<400> SEQUENCE: 4

Met Ala Asn Tyr Lys Lys Pro Lys Leu Leu Tyr Cys Ser Asn Gly Gly
1               5                   10                  15

His Phe Leu Arg Ile Leu Pro Asp Gly Thr Val Asp Gly Thr Arg Asp
                20                  25                  30

Arg Ser Asp Gln His Ile Gln Leu Gln Leu Ser Ala Glu Ser Val Gly
            35                  40                  45

Glu Val Tyr Ile Lys Ser Thr Glu Thr Gly Gln Tyr Leu Ala Met Asp
        50                  55                  60

Thr Asp Gly Leu Leu Tyr Gly Ser Gln Thr Pro Asn Glu Glu Cys Leu
65                  70                  75                  80

Phe Leu Glu Arg Leu Glu Glu Asn His Tyr Asn Thr Tyr Ile Ser Lys
                85                  90                  95

Lys His Ala Glu Lys Asn Trp Phe Val Gly Leu Asn Lys Asn Gly Ser
                100                 105                 110

Cys Lys Arg Gly Pro Arg Thr His Tyr Gly Gln Lys Ala Ile Leu Phe
            115                 120                 125

Leu Pro Leu Pro Val Ser Ser Asp
        130                 135
```

FGF HAVING ENHANCED STABILITY

CROSS-REFERENCE TO RELATED APPLICATIONS

This application claims priority to U.S. Provisional Patent Application No. 61/576,803 filed Dec. 16, 2011, which is incorporated by reference herein in its entirety.

STATEMENT REGARDING FEDERALLY SPONSORED RESEARCH OR DEVELOPMENT

This invention was made with government support under ES017166 and GM081629 awarded by the National Institutes of Health. The government has certain rights in the invention.

BACKGROUND

The invention relates generally to methods and compositions for culturing human pluripotent stem cells, and, more particularly, to methods and compositions having thermostable fibroblast growth factor (FGF) proteins for improved culture efficiency.

Human pluripotent cells, such as human embryonic stem (ES) cells and human induced pluripotent stem (iPS) cells have the potential to proliferate indefinitely and to differentiate into cells of all three germ layers (Lowry et al., PNAS 105: 2883-2888, 2008; Park et al., Nature 451:141-U141, 2008; Reubinoff et al., Nat. Biotechnol. 18:399-404, 2000; Takahashi et al., Cell 131:861,872, 2007; Thomson et al., Science 282:1145-1147, 1998; Yu et al., Science 318:1917-1920, 2007). These properties make human pluripotent cells invaluable for studying embryogenesis, for drug discovery, and for clinical applications.

Current in vitro culture methods for human ES and iPS cells require the addition of exogenous growth factors (Amit et al., Nat. Rev. Drug Discov. 8:235-253, 2004; Ludwig et al., Nat. Biotechnol. 24:185-187, 2006; Sato et al., Nat. Med. 10:55-63, 2004; Vallier et al., J. Cell Sci. 118:4495-4509, 2005; Wang et al., Blood 110:4111-4119, 2007). It is presently thought that three growth factors are sufficient to maintain pluripotency and self-renewal of human ES and iPS cells through activation of the FGF, TGF/Nodal, and Insulin/IGF pathways (Bendall et al., Nature 448:1015-1021 (2007); Eiselleova et al., Stem Cells 27:1847-1857 (2009); Vallier et al., J. Cell Sci. 118:4495-4509 (2005)).

The FGF pathway has been implicated in many stages of human pluripotent cell regulation, cell survival, proliferation, pluripotency, and lineage determination during differentiation (Eiselleova et al., Stem Cells 27:1847-1857, 2009; Lanner and Rossant, Development 137:3351-3360, 2010; Levenstein et al., Stem Cells 24:568-574, 2006; Vallier et al., J. Cell Sci. 118:4495-4509, 2005; Xu et al., Nat. Meth. 2:185-190, 2005). The FGF pathway is activated through the binding of FGF proteins to FGF receptors, which triggers MAP kinase cascades to regulate downstream events (Lanner and Rossant, 2010).

FGF-1-9 are 150-250 amino acid proteins with approximately 30-70% sequence homology in their 120-amino acid core region (Ornitz et al., Genome Biol. 2:3005.1-3005.12 (2001); Itoh et al., Trends Genet. 20:563-569 (2004)). Because of their substantial sequence homology, new members of the FGF family were identified in several species, from *Caenorhabditis elegans* to *Homo sapiens* (Itoh et al.), using homology-based methods. Twenty-two FGF family members have been identified in humans and mice (Ornitz et al., 2001; Itoh et al., 2004).

While different FGF proteins are used for various applications in cell culture, qualitative differences in cell responses elicited by the various FGF proteins remain ill-defined and poorly understood. The functional difference between FGF proteins that can and cannot support human pluripotent stem cells might be attributable to (1) the different affinity of the various FGF proteins to each of the four FGF receptors (FGFR) that lead to the activation of specific pathways (Eswarakumar et al., Cytokine Growth Factor Rev. 16:139-149, 2005; Mohammadi et al., Cytokine Growth Factor Rev. 16:107-137, 2005; Zhang et al., J. Biol. Chem. 281:15694-15700, 2006); and (2) the differential expression of FGFs and FGFRs in specific tissues (Beenken and Mohammadi, Nat. Rev. Drug Discov. 8:235-253, 2009). However, these factors insufficiently explain the functional differences between FGF-2 and other FGF proteins in human ES cell culture.

FGF-2 is routinely used for human ES and iPS cell culture (Levenstein et al., Stem Cells 24:568-574, 2006). Interestingly, FGF-1 does not support hESC pluripotency or cell survival, even though FGF-1 targets the same set of receptors as FGF-2 (Zhang et al., J. Biol. Chem. 281:15694-15700, 2006).

While FGF-2 supports pluripotency in defined long-term human pluripotent cell cultures, high FGF-2 concentrations (e.g., 100 ng/ml) are required, which significantly increases culture cost. It has been suggested that high FGF-2 concentrations might be required to satisfy specific dose-dependent signaling thresholds, and to overcome obstacles such as protein degradation (Levenstein et al., Stem Cells 24:568-574, 2006). Heparin and heparan sulfate can facilitate binding between FGF and FGFR to stimulate downstream activation (Levenstein et al., Stem Cells 26:3099-3107, 2008; Mohammadi et al., Curr. Opin. Struct. Biol. 15:506-516, 2005). Heparin and heparan sulfate promote pluripotency (Fume et al., PNAS 105:13409-13414, 2008; Levenstein et al., Stem Cells 26:3099-3107, 2008), although it is unclear whether they do so via the FGF pathway. Heparin appears to increase the stability of FGF-1 and might be important in the formation of FGF-1-FGFR complexes (Zakrzewska et al., J. Biol. Chem. 284:25388-25403 (2009)). While FGF-2 from zebrafish is capable of supporting self-renewal (Ludwig et al., Nat. Meth. 3:637-646, 2006), effective mammalian FGFs that can be used as an alternative to mammalian wild type FGF-2 are not known. Thus, there is a need in the art for more efficient growth factors that can support human pluripotent stem cells in culture.

BRIEF SUMMARY

In a first aspect, the present invention is summarized as a method for culturing human pluripotent stem cells, comprising the step of culturing a human pluripotent stem cell in a medium comprising at least one thermostable fibroblast growth factor-one (FGF-1) that comprises amino acid substitutions at positions corresponding to positions 40, 47, and 93 of wildtype truncated FGF-1 (SEQ ID NO:2), wherein the medium comprising the thermostable FGF-1 is characterized by an enhanced ability to support pluripotency relative to a medium comprising truncated wild type FGF 1 (SEQ ID NO:2).

In some embodiments of the first aspect, the amino acid sequence of the thermostable FGF-1 further comprises an amino acid substitution within the heparin binding domain. In some embodiments, the amino acid substitution within the heparin binding domain is at position 112 of SEQ ID NO:2.

In some embodiments of the first aspect, the thermostable FGF-1 comprises the amino acid sequence of SEQ ID NO:3.

In other embodiments, the amino acid sequence of the thermostable FGF-1 consists of the amino acid sequence of SEQ ID NO:3.

In further embodiments of the first aspect, the thermostable FGF-1 comprises the amino acid sequence of SEQ ID NO:4. In some embodiments, the amino acid sequence of the thermostable FGF-1 consists of the amino acid sequence of SEQ ID NO:4.

In some embodiments of the first aspect, the human pluripotent stem cells to be cultured are human embryonic stem cells or human induced pluripotent stem cells.

In some embodiments of the first aspect, the medium to be used further comprises heparin.

In some embodiments of the first aspect, the concentration of the thermostable FGF-1 in the medium is less than 40 ng/ml (e.g., 10 ng/ml or less).

In a second aspect, the present invention is summarized as a fully-defined medium suitable for culturing human pluripotent cells in an undifferentiated state, the defined medium comprising a thermostable fibroblast growth factor-one (FGF-1) that comprises amino acid substitutions at positions corresponding to positions 40, 47, and 93 of wildtype truncated FGF-1 (SEQ ID NO:2).

In some embodiments of the second aspect, the thermostable FGF-1, present in the fully defined medium, further comprises an amino acid substitution corresponding to position 112 of the wild type FGF-1 (SEQ ID NO:2).

In some embodiments of the second aspect, the thermostable FGF-1 comprises the amino acid sequence of SEQ ID NO:3. In other embodiments, the amino acid sequence of the thermostable FGF-1 consists of the amino acid sequence of SEQ ID NO:3.

In some embodiments of the second aspect, the thermostable FGF-1 comprises the amino acid sequence of SEQ ID NO:4. In other embodiments, the amino acid sequence of the thermostable FGF-1 consists of the amino acid sequence of SEQ ID NO:4.

In some embodiments of the second aspect, the thermostable FGF-1 is provided in the fully defined medium at a concentration of less than 40 ng/ml (e.g., 10 ng/ml or less).

In a third aspect, the present invention is summarized as a composition comprising: a human pluripotent stem cell and a culture medium comprising a thermostable fibroblast growth factor-one (FGF-1) that comprises amino acid substitutions at positions corresponding to positions 40, 47, and 93 of wildtype truncated FGF-1 (SEQ ID NO:2), and wherein the culture medium comprising the thermostable FGF-2 is suitable for culturing the human pluripotent cell in an undifferentiated state, and is characterized by an enhanced ability to support pluripotency relative to a medium comprising a truncated wild type FGF-1 (SEQ ID NO:2).

In some embodiments of the third aspect, the thermostable FGF-1 in the composition further comprises an amino acid substitution within the heparin binding domain (e.g., at a position corresponding to position 112 of a truncated wild type FGF-1 (SEQ ID NO:2).

In some embodiments of the third aspect, the thermostable FGF-1 comprises the amino acid sequence of SEQ ID NO:3. In other embodiments, the amino acid sequence of the thermostable FGF-1 consists of the amino acid sequence of SEQ ID NO:3.

In some embodiments of the third aspect, the thermostable FGF-1 comprises the amino acid sequence of SEQ ID NO:4. In other embodiments, the amino acid sequence of the thermostable FGF-1 consists of the amino acid sequence of SEQ ID NO:4.

In a fourth aspect, the present invention is summarized as a method for differentiating a human pluripotent stem cell into a mesoderm lineage cell, where the method comprises the step of culturing the human pluripotent stem cell in a medium until the cell expresses mesoderm lineage markers, wherein the medium comprises BMP4 and a thermostable fibroblast growth factor-one (FGF-1) that comprises amino acid substitutions at positions corresponding to positions 40, 47, and 93 of wildtype truncated FGF-1 (SEQ ID NO:2), and wherein the medium comprising the BMP 4 and the thermostable FGF 1 is characterized by an enhanced ability to support differentiation of a human pluripotent stem cell into a mesoderm lineage cell relative to a medium comprising BMP4 and a truncated wild type FGF-1 (SEQ ID NO:2).

In some embodiments of the fourth aspect, the thermostable FGF-1 further comprises an amino acid substitution at a position corresponding to position 112 of the wild type truncated FGF-1 (SEQ ID NO:2).

In some embodiments of the fourth aspect, the thermostable FGF-1 comprises the amino acid sequence of SEQ ID NO:3. In other embodiments, the amino acid sequence of the thermostable FGF-1 consists of the amino acid sequence of SEQ ID NO:3.

In some embodiments of the fourth aspect, the thermostable FGF-1 comprises the amino acid sequence of SEQ ID NO:4. In other embodiments, the amino acid sequence of the thermostable FGF-1 consists of the amino acid sequence of SEQ ID NO:4.

In a fifth aspect, the present invention is summarized as a method for reprogramming a human somatic cell into a human pluripotent cell, where the method comprises culturing the somatic cell in a medium until the cell expresses markers indicative of a human pluripotent cell, wherein the medium comprises water, salts, amino acids, vitamins, a carbon source, insulin, selenium and at least one thermostable fibroblast growth factor-one (FGF-1) that comprises amino acid substitutions at positions corresponding to positions 40, 47, and 93 of wildtype truncated FGF-1 (SEQ ID NO:2), and wherein the medium comprising the thermostable FGF-1 is characterized by an enhanced ability to support pluripotency relative to a medium comprising a truncated wild type FGF-1 (SEQ ID NO:2).

In some embodiments of the fifth aspect, the thermostable FGF-1 further comprises an amino acid substitution at a position corresponding to position 112 of the wild type FGF-1 (SEQ ID NO:2).

In some embodiments of the fifth aspect, the thermostable FGF-1 comprises the amino acid sequence of SEQ ID NO:3. In other embodiments, the amino acid sequence of the thermostable FGF-1 consists of the amino acid sequence of SEQ ID NO:3.

In some embodiments of the fifth aspect, the thermostable FGF-1 comprises the amino acid sequence of SEQ ID NO:4. In other embodiments, the amino acid sequence of the thermostable FGF-1 consists of the amino acid sequence of SEQ ID NO:4. In further embodiments of the fifth aspect, the medium is serum-free. In other embodiments of the fifth aspect, the medium further comprises heparin.

The methods and compositions described herein are useful in a variety of applications, such as maintaining and passaging a viable population of human pluripotent stem cells, reprogramming human somatic cells into pluripotent stem cells, or differentiating human pluripotent stem cells along certain lineages, e.g., the mesodermal lineage, for which FGF is an important morphogen.

These and other features, objects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to preclude the invention from covering modifications, equivalents and alternatives. Reference should therefore be made to the claims recited herein for interpreting the scope of the invention.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 1A shows that ERK phosphorylation correlates with the activation of FGF receptors in human ES cells. H1 cells were incubated in $E_8$ media (Chen et al., Nat. Meth. 8:424-429, 2011) (100 ng/ml FGF-2 and 2 ng/ml Tgfβ) for 30 minutes with drug treatments (10 μM SU5402—FGFR inhibitor or 10 μM SB43542-TGFβ inhibitor, or both). Proteins were harvested to analyze ERK1/2 phosphorylation (pERK1/2) by western blot. FIG. 1B shows that inhibition of ERK phosphorylation suppresses NANOG expression; NANOG expression was measured after three days of incubation. FIG. 1C shows screening for FGFs supporting sustained ERK phosphorylation. H1 ES cells were plated into basic media ($E_8$ media without TGFβ) with different FGFs (100 ng/ml) for 24 hours, and proteins were then collected to detect ERK phosphorylation. FIG. 1D shows screening for FGFs supporting pluripotency. H1 cells were maintained in the same media as (C) for three days, cells were harvested to measure the expression of NANOG by RT-qPCR. GAPHD was used as control. FIG. 1E shows screening for FGFs that stimulate ERK phosphorylation in short exposure. Media used in (C) were applied for 15 minutes on FGF-starved ES cells before proteins were collected to analyze for ERK phosphorylation. FIG. 1F shows how thermostability of FGF affects activation of ERK phosphorylation. Media used in (C) were incubated at 37° C. for 6 hours, and then applied for 15 minutes on FGF-starved ES cells, before proteins were collected for ERK phosphorylation analysis.

FIG. 2A-C illustrates dynamic regulation to maintain FGF pathway activation at relatively low level. FIG. 2A shows that ERK phosphorylation decreases after initial activation. FGF-2 (100 ng/ml) was added to FGF-starved ES cells, and proteins were collected at specific time points for western blot. ERK phosphorylation was significantly lower than previous time points. FIG. 2B shows that there was no significant loss of FGF-2 activity in media at 12 hours. Growth media was collected from the cell culture and was applied to FGF-starved cells for 15 minutes and proteins were collected for western blot. FIG. 2C shows that ERK phosphorylation is controlled at a consistently moderate level in continuous FGF culture. FGF-2 was applied onto FGF-starved and FGF-primed cells, and cells were harvested at specific time points.

FIG. 3A-F Illustrates a thermostable FGF-1 mutant and its ability to support ERK phosphorylation and pluripotency. FIG. 3A shows that FGF-1 is unstable at 37° C. Media with FGF-1 were incubated with heparin at 37° C., and then applied for 15 minutes on FGF-starved ES cells at specific time points, before proteins were collected to analyze for ERK phosphorylation. FIG. 3B shows FGF-1 protein mutated to increase thermostability or heparin affinity. The mutated amino acid is underlined (Zakrzewska et al., J. Mol. Biol. 352:860-875, 2005; Zakrzewska et al., J. Biol. Chem. 284:25388-25403, 2009). FIG. 3C shows that mutations to FGF-1 improved maintenance of ERK phosphorylation for 24 hours. H1 ES cells were plated into basic media ($E_8$ media without TGFβ) with different FGFs (100 ng/ml) for 24 hours, and proteins were then collected to detect ERK phosphorylation. FIG. 3D shows an FGF-1 mutant FGF-1 4X (Q40P, S47I, H93G, with K112N) that is thermostable, while FGF-1 3X (Q40P, S47I, H93G) and FGF-2 were stabilized by heparin. Media with different FGFs were pre-incubated at 37° C. for 24 hours, and then applied for 15 minutes on FGF-starved ES cells, before proteins were collected to analyze for ERK phosphorylation. FIG. 3E shows that mutated FGF-1 supports ES cell growth. H1 cells were maintained in $E_8$ media with different FGFs, and cells were counted after 96 hours. FIG. 3F shows that mutated FGF-1 supports pluripotency of human ES cells. H1 cells were maintained in E8 media without TGFβ and different FGFs, and OCT4 expression was analyzed after 2 passages.

FIG. 4A-E illustrates stabilized FGF proteins. FIG. 4A shows that FGF-1 and heparin help maintain ES cell morphology. H1 cells were cultured in specific media for 5 days. FIG. 4B shows FGF-2 and FGF-1 derivatives purified from *E. coli* stained with Coomassie Blue following PAGE electrophoresis. FIG. 4C shows that mutations did not affect FGF activity significantly. Same amount of FGFs (10 ng/ml) was applied onto FGF-starved cells for 15 minutes and protein was harvested to measure ERK phosphorylation. FIG. 4D shows that FGF-1 3X cultured in $E_8$ (TGFβ) media sustained long-term ES cell culture. OCT4 staining was performed after 3 passages. ES cells were maintained in FGF-1 3X media for 10 passages, and cells maintained normal karyotype. FIG. 4E shows that full-length and truncated FGF-1s lost their activity after 6-hour incubation at 37° C., and heparin failed to preserve the activity. Media with full-length FGF-1 or truncated FGF-1 were treated with or without heparin at 37° C. for 6 hours and were then applied to FGF-starved ES cells for 15 minutes. Protein was harvested to measure ERK phosphorylation.

FIG. 5 A-D illustrates that FGF stability affects differentiation and reprogramming

Figure 1A:
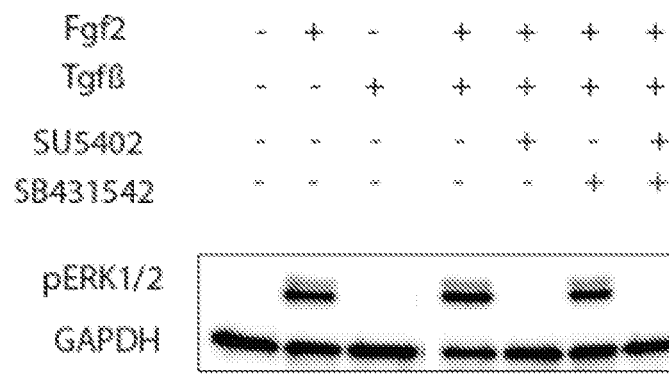
FIG. 1A-F illustrates that thermostability of FGF affects its ability to stimulate ERK phosphorylation.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

The invention relates to the use of variants of FGF-1 having enhanced thermostability to improve maintenance of pluripotency of cultured human pluripotent stem cells, or to enhance their differentiation into certain lineages (e.g., mesoderm) when FGF is one of the morphogens used in the differentiation.

The present invention relates to the inventors' observation that protein stability of FGF-family proteins plays an essential role in the molecule's ability to support human pluripotent cell cultures. The invention provides thermostable FGF-1 compositions, and methods to support human pluripotent stem cells in an undifferentiated state. In some instances, the stability and effectiveness in supporting pluripotency of the thermostable FGF-1 can be further enhanced by heparin binding to the thermostable FGF-1.

Many FGF-family members, such as FGF-1, have repeatedly been shown to fail to maintain human pluripotent stem cells in culture, for unknown reasons. The invention presented herein demonstrates, for the first time, that thermostability of FGF-1 can be a determining aspect of growth factor regulation in stem cell biology. The disclosed invention also demonstrates, for the first time, that amino acid substitutions in wild type FGF-1 that result in thermostable FGF-1 sequence variants have superior abilities to maintain pluripotency in long-term and under feeder independent conditions. Unexpectedly, these FGF-1 sequence variants can also act as effective morphogens to induce certain lineage-specific differentiation, and to enhance somatic cell reprogramming.

Thermoinstability of FGF-1 was not an obvious cause of wildtype FGF-1's failure to support human pluripotent stem cells in culture because the role of numerous characteristics of FGF-1 biology in maintaining pluripotency were unknown. FGF receptors in different cell types respond to FGF ligands differently. Without directly testing the influence of individual FGF variants on human ES cell growth and maintenance, the skilled artisan could not have predicted which FGF variants could support pluripotency. Indeed, in view of the studies carried out on other cell types, and the fact that all FGF receptors are expressed in hES cells, the skilled artisan would have predicted that every FGF should have the capacity to support pluripotency of hES or hiPS cells, which is not, in fact, the case.

I. Definitions

As used herein, "defined culture medium," "defined medium," or "fully defined medium" refers to an essentially serum-free medium that has known quantities of all ingredients.

As used herein, "enhanced ability to support pluripotency" means that a lower concentration of the thermostable FGF-1 can support maintenance of pluripotency in vitro, compared to the concentration of other FGFs known to support pluripotency, and compared to FGFs, such as wild type FGF-1, that do not support pluripotency. To confirm whether a thermostable FGF supports pluripotency, 5 passages (~20-30 days) in culture media containing the thermostable FGF is usually required, wherein cells maintain morphology and genetic expression characteristic of human pluripotent cells. For example, human pluripotent cells typically exhibit a round shape, large nucleoli and scant cytoplasm and express OCT4. Thermostable FGF-1 can also support pluripotency of human pluripotent cells in vitro for a longer period of time (e.g., greater than 48 hours) compared to wildtype FGF-2, which is effective for less than 24 hours.

As used herein, "iPS cells" refer to cells that are substantially genetically identical to their respective differentiated somatic cell of origin and display characteristics similar to human ES cells, as described herein. The cells can be obtained from various differentiated somatic cells, e.g., mononuclear blood cells, skin fibroblasts, keratinocytes, etc.

As used herein, "serum-free" means that neither the culture nor the culture medium contains serum or plasma, although purified or synthetic serum or plasma components (e.g., FGFs) can be provided in the culture in reproducible amounts as described below. For example, an essentially serum-free medium can contain less than about 1% serum or serum replacement.

As used herein, thermostable "FGF-1," refers to an FGF-1 having an amino acid sequence that includes the amino acid sequence of SEQ ID NO:2 (a truncated wildtype FGF-1), but having amino acid substitutions at at least three positions: 40, 47, and 93 relative to SEQ ID NO:2, and retaining the ability to stimulate ERK phosphorylation in human pluripotent stem cells after a 24 hour incubation period with a given amount of the thermostable FGF-1. In some cases, the thermostable FGF-1 also includes a fourth amino acid substitution, which falls in the heparin binding domain of truncated FGF-1, e.g., position 112.

As used herein, "wild type amino acid sequence" refers to the most common amino acid sequence among members of a species.

As used herein, "thermostable FGF-1" refers to an FGF-1 protein having an altered amino acid sequence relative to the wild type FGF-1 sequence that is also more stable than wild type FGF-1 under human pluripotent stem cell culture conditions. As disclosed herein, binding of wild type FGF-1 to heparin or FGF-binding protein (FGFP) enhances its thermostability but fails to render FGF-1 capable of long-term undifferentiated human pluripotent cell culture. In the context of this application, a wild type FGF-1 protein bound to heparin, even if more stable to heat than unbound FGF-1, is not encompassed by the term "thermostable FGF."

II. Methods

The invention provides a method for culturing human pluripotent stem cells in culture. Human pluripotent stem cells, such as human embryonic stem cells or induced pluripotent stem cells, are cultured in a medium containing a thermostable FGF-1.

In some embodiments, human pluripotent stem cells, such as human embryonic stem cells or human induced pluripotent cells, are cultured in a medium containing at least one thermostable FGF-1. The thermostable FGF-1 sequence variants described herein are characterized by an enhanced ability, compared to the respective wild type FGF-1 protein, to support pluripotency of cultured human pluripotent stem cells over time, such as several weeks and passages, in culture. Methods for introducing single or multiple changes into the amino acid sequence of an FGF protein are well known in the art (e.g., Kim et al. J. Mol. Biol. 328(4): 951-961 (2003); Brych et al. J. Mol. Biol. 344(3): 769-780 (2004); Lee et al., J. Mol. Biol. 393(1): 113-127 (2009); Zakrzewska et al., J. Mol. Biol. 352(4): 860-875 (2005); Zakrzewska et al., Protein Eng. Des. Sel17(8): 603-611 (2004); Zakrzewska et al., J. Biol. Chem. 284(37): 25388-25403 (2009); U.S. Pat. No. 7,659,379, each of which is incorporated herein by reference as if set forth in its entirety).

In some embodiments, the thermostable FGF-1 used in the method comprises the amino acid sequence of a thermostable fibroblast growth factor-one (FGF-1) that comprises amino acid substitutions at positions corresponding to positions 40, 47, and 93 of wildtype truncated FGF-1 (SEQ ID NO:2), wherein the medium comprising the thermostable FGF-1 is characterized by an enhanced ability to support pluripotency relative to a medium comprising truncated wild type FGF-1 (SEQ ID NO:2). The nomenclature of the FGF-1 sequence variants disclosed herein follows the truncated FGF-1 naming convention, following the numbering convention established by Gimenez-Gallego et al., Biochem. Biophys. Res. Comm. 128 611-617 (1986).

In some embodiments, the thermostable FGF-1 to be used includes the amino acid sequence shown in SEQ ID NO:3 ("FGF1-3X"), which contains Q40P, S47, and H93 mutations. Optionally, the thermostable FGF-1 to be used in the method can further include a single amino acid substitution within the heparin binding domain of the thermostable FGF-1. The skilled artisan would have found it counterintuitive to introduce a mutation in the heparin binding domain because binding to heparin enhances stability of FGF-1 and -2 at 37° C. In some embodiments, the amino acid substitution in the heparin binding domain is at position 112 relative the amino acid sequence of truncated wild type FGF-1 (position 127 in full length, wildtype FGF-1), as shown in SEQ ID NO:2. K112 (K127 in full length FGF-1) is the amino acid that significantly contributes to heparin binding (Zakrzewska et al., J. Biol. Chem. 284:25388-25403, 2009). In one embodiment, the amino acid substitution at position 112 is a K112N substitution.

In other embodiments, the thermostable FGF-1 to be used in the method includes the amino acid sequence shown in SEQ ID NO:4 ("FGF1-4X"), which contains four amino acid substitutions: Q40P, S47, H93, and K112N. In some embodiments, the thermostable FGF-1 to be used includes the amino acid sequence of SEQ ID NO:3 or SEQ ID NO:4, but is greater in length than either of these amino acid sequences (e.g., an N-terminal or C-terminal fusion polypeptide). For example, in some cases, the thermostable FGF-1 to be used, in addition to the amino acid sequence of SEQ ID NO:3 or SEQ ID NO:4 also includes the full length amino terminal sequence of human wildtype FGF-1. polypeptide thermostable FGF-1 to be used is a full length human FGF-1 comprising the amino acid sequence of SEQ ID NO:3. include a mutation In one embodiment, the thermostable FGF-1. In other embodiments, the amino acid sequence of the thermostable FGF-1 consists only of the amino acid sequence of the truncated human FGF-1 sequence variant of SEQ ID NO:3 or SEQ ID NO:4.

In some embodiments, in addition to a thermostable FGF-1, heparin is also included in the medium used in the culture method. A suitable concentration of heparin ranges from about 50 ng/ml to about 200 ng/ml, e.g., about 60 ng/ml, 75 ng/ml, 90 ng/ml, 100 ng/ml, 125 ng/ml, 150 ng/ml, 175 ng/ml, or another concentration of heparin from about 50 ng/ml to about 200 ng/ml.

A medium used in the methods to culture and maintain human pluripotent stem cells, as described herein, can be any medium that supports human pluripotent cells in culture (e.g., Chen et al., Nat. Meth. 8:424-429, 2011 or any of the commercial media mentioned herein), but in which a thermostable FGF-1 is substituted, at least in part, for an FGF (e.g., FGF-2) normally used in the completed culture medium (e.g., mTeSR®). In some embodiments, thermostable FGF-1 is the only FGF-1 used in the medium used in the culturing method, i.e., it is substituted in commercial media that are typically pre-formulated with wild type FGF-2. In other embodiments, the medium to be used might may contain 20%, 40%, 60%, 80% or 99% thermostable FGF-1 (e.g., thermostable FGF1-4X) and the balance being wild type FGF-2. Preferably, the medium is fully defined.

Preferably, the thermostable FGF-1 concentrations used to support pluripotency are lower than for wild type FGF-1 proteins. For example, a thermostable FGF-1 supports pluripotency at concentrations lower than those required for FGF-1 bound to heparin or for FGF-2. Specifically, an exemplified thermostable FGF-1 sequence variant, FGF1-4X (SEQ ID NO:4), with 4 amino acid mutations, Q40P, S47I, H93G, and K112N relative to SEQ ID NO: 2, as exemplified herein, can support self-renewal of human pluripotent ES and iPS cells at concentrations 4 to 10-fold lower than those ordinarily used for FGF-2 (about 40-100 ng/ml).

In some embodiments of the invention, human pluripotent cells are cultured with a thermostable FGF-1 at a concentration of 40 ng/ml or less, preferably 10 ng/ml or less, 3 ng/ml or less, or 1 ng/ml or less. It is contemplated that culture conditions including a thermostable FGF-1 (e.g., FGF1-3X or FGF1-4X) at a concentration of 40 ng/ml or less, preferably 10 ng/ml, 3 ng/ml, or 1 ng/ml or less, are sufficient for maintaining human pluripotent cells and for reprogramming somatic cells into induced human pluripotent cells. In some embodiments, FGF1-3X or FGF1-4X are included at a concentration of about 10 ng/ml to about 50 ng/ml, 10 ng to about 30 ng/ml, 3 ng/ml to about 10 ng/ml, 1 ng/ml to about 3 ng/ml, or about 0.2 ng/ml to about 1 ng/ml.

To confirm that a particular thermostable FGF-1 sequence variant can support pluripotency, human pluripotent cells are cultured in a medium containing the thermostable FGF-1 for at least 5 passages (~20-30 days) and then evaluated for pluripotency. Criteria for evaluating pluripotency of human pluripotent stem cells are known in the art, and include, but are not limited to, expression of Oct4 and Nanog mRNA and protein, and suppression of differentiation markers (e.g., Hand1 and Gata). The function of FGF-2 in human pluripotent stem cells can be conveniently assessed using a biochemical endpoint such as ERK phosphorylation. Measuring increased ERK phosphorylation in response to FGF stimulation, as described herein, provides a rapid measure of the ability of a thermostable FGF-2 to support in vitro pluripotency. Other methods of assessing pluripotency are also suitable.

The invention is also directed at a method for reprogramming human somatic cells into human induced pluripotent (iPS) cells in culture. Somatic cells, such as foreskin fibroblast cells, are cultured in a medium containing a thermostable FGF-1, as described herein, e.g., in the presence of FGF1-4X, FGF1-3X, or a combination thereof. Suitable culture media (buffered to a pH of about 7.4) for reprogramming human somatic cells, in addition to a thermostable FGF-1, as described herein, include water, salts, amino acids, vitamins, a carbon source, insulin, and selenium. The medium can be any medium that supports human pluripotent cells in culture (e.g., Chen et al., Nat. Meth. 8:424-429, 2011). Preferably, the medium is fully defined. The medium can be any of the above-mentioned media that support pluripotency of human pluripotent stem cells. Preferably, the medium to be used is fully defined, e.g., E8 medium. Human somatic cells can be reprogrammed using methods known in the art (e.g., Patent Application Publication Nos. 2008/0233610 and 2010/0184227, each incorporated herein by reference in its entirety as if set forth herein. A medium containing a thermostable FGF-1 is suited for use in other reprogramming methods, such as those mentioned below (and, likewise, each incorporated by reference herein in its entirety): Adenoviral vector reprogramming (Zhou and Freed, Stem Cells 27: 2667-2674, 2009); Sendai virus reprogramming (Fusaki et al., Proc Jpn Acad 85: 348-362, 2009); polycistronic minicircle vector reprogramming (Jia et al., Nat Methods 7: 197-199, 2010); piggyBac transposon reprogramming (Woltjen et al., Nature 458: 766-770, 2009; Yusa et al., Nat Methods 6: 363-369, 2009); recombinant proteins for reprogramming (Zhou et al., Cell Stem Cell 4: 381-384, 2009); whole cell extracts isolated from human ES cells (Cho et al., Blood 116: 386-395, 2010) or genetically engineered HEK293 cells (Kim et al., Cell Stem Cell 4: 472-476, 2009); small molecules to replace individual reprogramming factors (Desponts and Ding, Methods Mol Biol 636: 207-218, 2010; Li and Ding, Trends Pharmacol Sci 31: 36-45, 2010). Suitable human somatic cells for reprogramming include, but are not limited to, blood mononuclear cells, skin-derived fibroblasts, and keratinocytes.

The invention is also directed to a method for differentiating a human pluripotent stem cell into a mesoderm lineage cell, where the method includes culturing human pluripotent stem cells in a medium until the cultured cells express mesoderm lineage markers, wherein the medium comprises BMP4 and a thermostable FGF-1 comprising the amino acid sequence of a thermostable fibroblast growth factor-one (FGF-1) that comprises amino acid substitutions at positions corresponding to positions 40, 47, and 93 of wildtype truncated FGF-1 (SEQ ID NO:2), and wherein the medium comprising the BMP4 and the thermostable FGF-1 is characterized by an enhanced ability to support differentiation of a human pluripotent stem cell into a mesoderm lineage cell relative to a medium comprising BMP4 and a truncated wild type FGF-1 (SEQ ID NO:2).

Suitable media for mesodermal differentiation, include any of the thermostable FGF-1-containing media described herein (e.g., E8 medium plus FGF1-4X) plus an appropriate concentration of BMP4, which may range from about 2 ng/ml to about 10 ng/ml, e.g., about 3 ng/ml, 5 ng/ml, 7 ng/ml, 8 ng/ml or another concentration of BM4 from about 2 ng/ml to about 10 ng/ml. Markers for assessing mesoderm lineage differentiation include, but are not limited to, Brachyury (T), WNT3, and MIXL1.

III. Compositions

The invention is also directed to a fully-defined medium suitable for culturing human pluripotent stem cells in an undifferentiated state throughout several passages, the medium containing at least one thermostable FGF-1 having enhanced ability to support pluripotency, as described herein. Culture conditions that permit the long-term culture of undifferentiated human pluripotent cells in a defined medium supplemented with high concentrations of FGF-2, e.g., 100 ng/ml, are known in the art (e.g., Ludwig et al., Nat. Methods 3:637-646 (2006), incorporated herein by reference as if set forth in its entirety). It is specifically contemplated that the fully-defined medium described herein contains at least one thermostable FGF-1 at a concentration lower than that required of wild type FGF-2 protein, wherein the lower concentration is at least 5% lower than that required of wild type FGF-2 protein, preferably at least 10% lower than that required of wild type FGF-2 protein, more preferably at least 15%, 20%, 30%, 40%, 50%, or at least 60% lower than that required of wild type FGF-2 protein.

In some embodiments, the medium contains a thermostable FGF-1 instead of, or in addition to, wild type FGF-2. In a preferred embodiment, this medium is suitable for the derivation of human ES cell lines and reprogramming of somatic cells. Use of this medium in methods for differentiating human pluripotent stem cells, such as into cells of the mesoderm lineage, and in methods of reprogramming somatic cells into iPS cells, is specifically contemplated, as described herein.

In some embodiments, the fully defined medium includes a thermostable fibroblast growth factor-one (FGF-1) that comprises amino acid substitutions at positions corresponding to positions 40, 47, and 93 of wildtype truncated FGF-1 (SEQ ID NO:2), wherein the medium comprising the thermostable FGF-1 is characterized by an enhanced ability to support pluripotency relative to a medium comprising truncated wild type FGF-1 (SEQ ID NO:2).

In some embodiments, the fully defined medium includes a thermostable FGF-1 comprising the amino acid sequence shown in SEQ ID NO:3 ("FGF1-3X"), which contains Q40P, S47, and H93 mutations. Optionally, the medium can include a thermostable FGF-1 that has a single amino acid substitution within the heparin binding domain of the thermostable FGF-1. In some embodiments, the amino acid substitution in the heparin binding domain is at position 112 relative the amino acid sequence of truncated wild type FGF-1 (position 127 in full length, wildtype FGF-1), as shown in SEQ ID NO:2. In one embodiment, the amino acid substitution at position 112 is a K112N substitution.

In other embodiments, the thermostable FGF-1 to be used in the method includes the amino acid sequence shown in SEQ ID NO:4 ("FGF1-4X"), which contains four amino acid substitutions: Q40P, S47, H93, and K112N. In some embodiments, the thermostable FGF-1 in the fully defined medium includes the amino acid sequence of SEQ ID NO:3 or SEQ ID NO:4, but is greater in length than either of these amino acid sequences (e.g., an N-terminal or C-terminal fusion polypeptide). For example, in some cases, the thermostable FGF-1 to be used, in addition to the amino acid sequence of SEQ ID NO:3 or SEQ ID NO:4 also includes the full length amino terminal sequence of human wildtype FGF-1 (i.e., amino acids 3-21 are retained). polypeptide thermostable FGF-1 to be used is a full length human FGF-1 comprising the amino acid sequence of SEQ ID NO:3. include a mutation In one embodiment, the thermostable FGF-1. In other embodiments, the amino acid sequence of the thermostable FGF-1 consists only of the amino acid sequence of the truncated human FGF-1 sequence variant of SEQ ID NO:3 or SEQ ID NO:4.

In some embodiments, where the medium contains a thermostable FGF1-3X (SEQ ID NO:3), heparin is also included in the medium. A suitable concentration of heparin ranges from about 50 ng/ml to about 200 ng/ml, e.g., about 60 ng/ml, 75 ng/ml, 90 ng/ml, 100 ng/ml, 125 ng/ml, 150 ng/ml, 175 ng/ml, or another concentration of heparin from about 50 ng/ml to about 200 ng/ml.

The invention is also directed at a composition that contains human pluripotent stem cells (e.g., human embryonic stem cells or human induced pluripotent stem cells), and any of the thermostable FGF-1-containing media described herein that is suitable for maintaining pluripotency of human pluripotent stem cells.

The invention will be more fully understood upon consideration of the following non-limiting Examples. All papers and patents disclosed herein are hereby incorporated by reference as if set forth in their entirety.

EXAMPLES

Example 1

Variable FGF Pathway Activation in Human Pluripotent Stem Cells by FGF Family Members Cell Culture Human ES cells were maintained in specific media on matrigel-coated tissue culture plates essentially as described previously (Ludwig et al., Nat. Meth. 3:637-646, 2006). Cells were passaged with EDTA essentially as described previously (Chen et al., Cell Stem Cell 7:240-248, 2010). Briefly, cells were washed twice with PBS/EDTA medium (0.5 mM EDTA in PBS, osmolarity 340 mOsm), then incubated with PBS/EDTA for 5 minutes at 37° C. The PBS/EDTA was removed, and the cells were washed swiftly with a small volume of medium.

Cell Growth Measurement

Cell growth was analyzed essentially as described previously (Chen et al., Cell Stem Cell 7:240-248, 2010). E8 cell culture medium was used for cell growth experiments (Chen et al., Nat. Meth. 8:424-429, 2011). All experiments were performed in triplicate using 12-well plates. Prior to the addition of cells, 500 μA medium was loaded into each well. Cells were dissociated for 5 minutes or until fully detached from the plate with TrypLE (LIFE TECHNOLOGIES), which was subsequently neutralized with equal volumes of media. The cells were counted, washed, and diluted to concentrations of 100,000 to 300,000 cells/ml and 100 μl of the cell solution was added into each well. At various time points, cells were again dissociated with 0.4 ml TrypLE, neutralized with equal volumes of 10% FBS in DMEM, and counted using flow cytometry. Approximately 500 count-bright beads (LIFE TECHNOLOGIES) were added to each sample as an internal control and 200 beads were counted for each sample. For proliferation experiments, media were changed daily up to the day of analysis, and cells were counted as described above.

FGF Expression and Purification

FGF proteins were expressed in ROSETTA™ 2 (DE3) pLysS cells (NOVAGEN®) using MAGICMEDIA® (LIFE TECHNOLOGIES) at 37° C. for 24 hours. FGF proteins were purified essentially as described by Wiedlocha et al., Mol. Cell. Biol. 16(1): 270-280 (1996), incorporated herein by reference as if set forth in its entirety. Briefly, bacterial pellets were sonicated and centrifuged. The clear supernatant was applied to a heparin cartridge (BIO-RAD) equilibrated with 0.5 M NaCl in 20 mM sodium phosphate (pH 7.5)-1 mM EDTA-1 mM dithiothreitol. Fusion proteins were eluted with 1 M NaCl in the same buffer and dialyzed against 20 mM sodium phosphate (pH 8.0)-1 mM EDTA-1 mM dithiothreitol. Subsequently, the fusion proteins were applied to a Q cartridge (BIO-RAD) and eluted with a linear NaCl gradient in the same buffer.

FGF-1 derivatives were generated in the form of truncated FGF-1, wherein the first 19 of 21 (positions 3-21) amino acid residues were deleted.

Figure 1B:
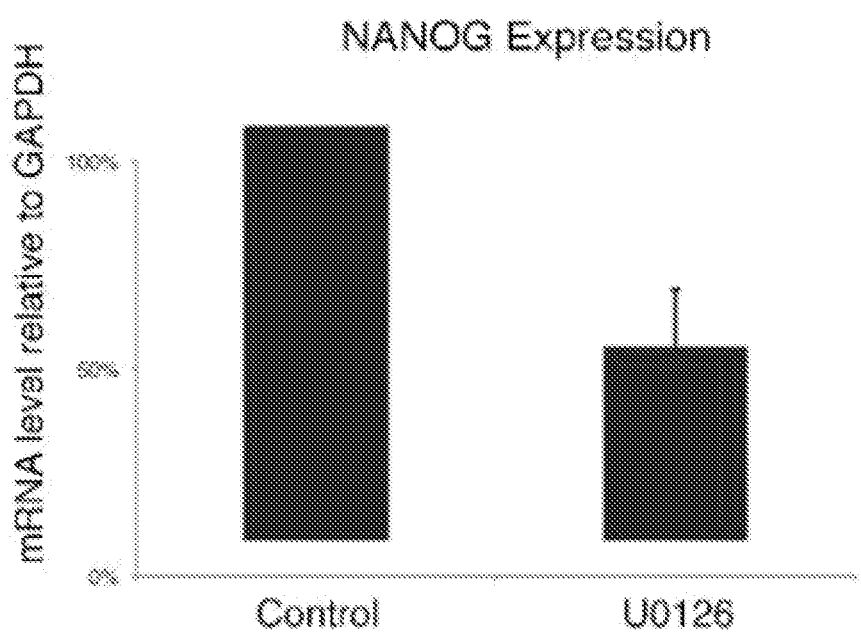
Figures 1C, 1D:
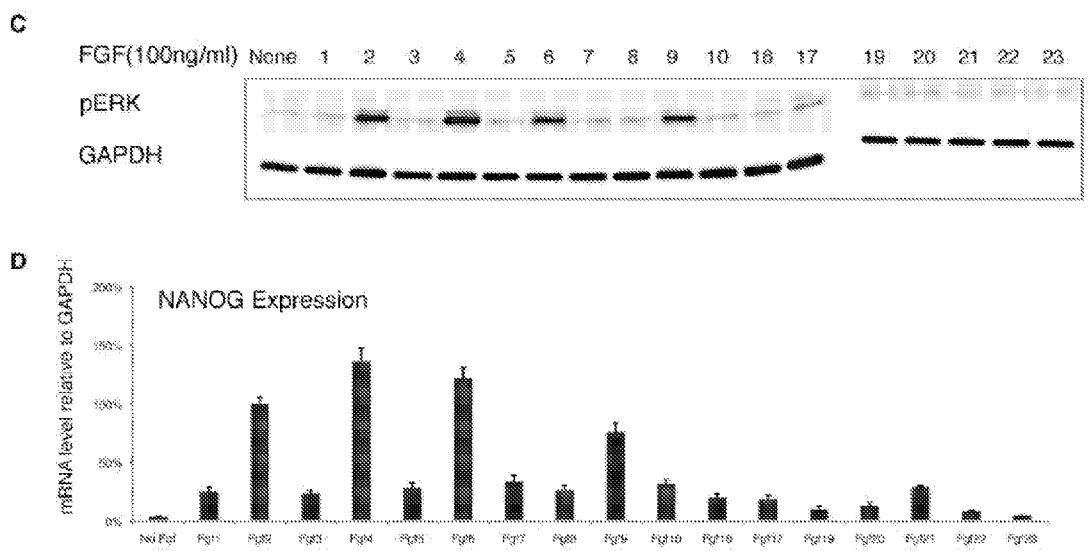
Figure 1E:
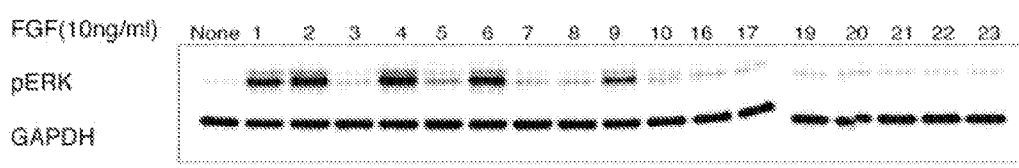
Figure 1F:

Pluripotency of human ES and iPS cells is supported by FGF and TGFβ/NODAL pathways (Vallier et al., J. Cell Sci. 118:4495-4509, 2005). FGF-2, not TGFβ, stimulates MAP kinase ERK1/2 phosphorylation after short-term incubation (15 minutes) (FIG. 1A). At the same time, ERK inhibition suppresses expression of pluripotency marker genes, such as NANOG (FIG. 1B). Cell culture experiments showed that an increase in extracellular signal-regulated kinase (ERK) phosphorylation in ES cells can be used as reliable indicator of FGF pathway activation. Using ERK phosphorylation and NANOG expression to determine the function of the various FGF family members on human pluripotent stem cells revealed that only FGF-2, FGF-4, FGF-6, and FGF-9 were able to sustain strong ERK phosphorylation after 24 hours in cell culture (FIG. 1C). These results were consistent with NANOG expression in response to the various FGFs in ES cells (FIG. 1D). However, 15 minute incubations with the various FGF family members led to different ERK phosphorylation patterns (FIG. 1E). Strong ERK phosphorylation induced by FGF-1, FGF-2, FGF-4, FGF-6, and FGF-9 correlated with the respective FGF's ability to bind to FGF-1R. FGF-1 was able to induce ERK phosphorylation but this activity was lost within about six hours of incubation at 37° C. (FIG. 1F). These results indicate that FGF-1 is not as stable at 37° C. relative to other FGF proteins, such as FGF-2 and FGF4, which might contribute to its inability to maintain ERK phosphorylation and pluripotency in human ES cells.

Example 2

Thermostable FGF-1 Supports Pluripotency of Human ES Cells in Vitro

To determine how the function of FGF proteins can be affected by thermostability, above and beyond ligand-specificity, FGF-1 was used as a model protein. FGF-1 is not stable at 37° C. and does not support self-renewal of human ES cells (FIG. 1). Frequent addition of medium containing FGF-1 and addition of heparin significantly improved short-term cell culture (FIG. 2A). Nevertheless, FGF-1 activity was largely lost after 6 hours at 37° C., even in the presence of heparin (FIG. 3A). Truncated FGF-1 protein, which is widely available, was also unstable at 37° C. and exhibited thermostability dynamics similar to full length FGF1 (FIG. 4E), suggesting that the N-terminal sequence of FGF-1 does not play an important role in thermostability.

To determine if FGF-1 stability contributes, at least in part, to the rapid loss of FGF-1 activity, several FGF-1 mutants were analyzed for their ability to support ES cells. The amino acid sequence of these mutant FGF-1 proteins affects their stability or their ability to bind heparin but not their ability to bind FGF receptors (Zakrzewska et al., J. Mol. Biol. 352:860-875, 2005; Zakrzewska et al., J. Biol. Chem. 284:25388-25403, 2009) (FIG. 3B and FIG. 4B). The Lysine residue at position 112 (K112) of FGF-1 is important for heparin binding. An amino acid other than lysine at position 112, e.g., asparagine (K112N), results in weak heparin affinity. Glutamine at position 40 (Q40), serine at position 47 (S47), and histidine at position 93 (H93) of FGF-1 are not exposed to the folded protein surface, but contribute to thermal instability. Mutation of all three positions (e.g., Q40P, S47I, and H93G) results in a protein (FGF-1 3X) having enhanced thermostability. Mutation of all four positions (e.g., Q40P, S47I, H93G, and K112N) results in a protein (FGF-1 4X, FIG. 3B) that is at least as stable as FGF-1 bound with heparin (Zakrzewska, J. Biol. Chem. 284:25388-25403, 2009).

Figure 4D:
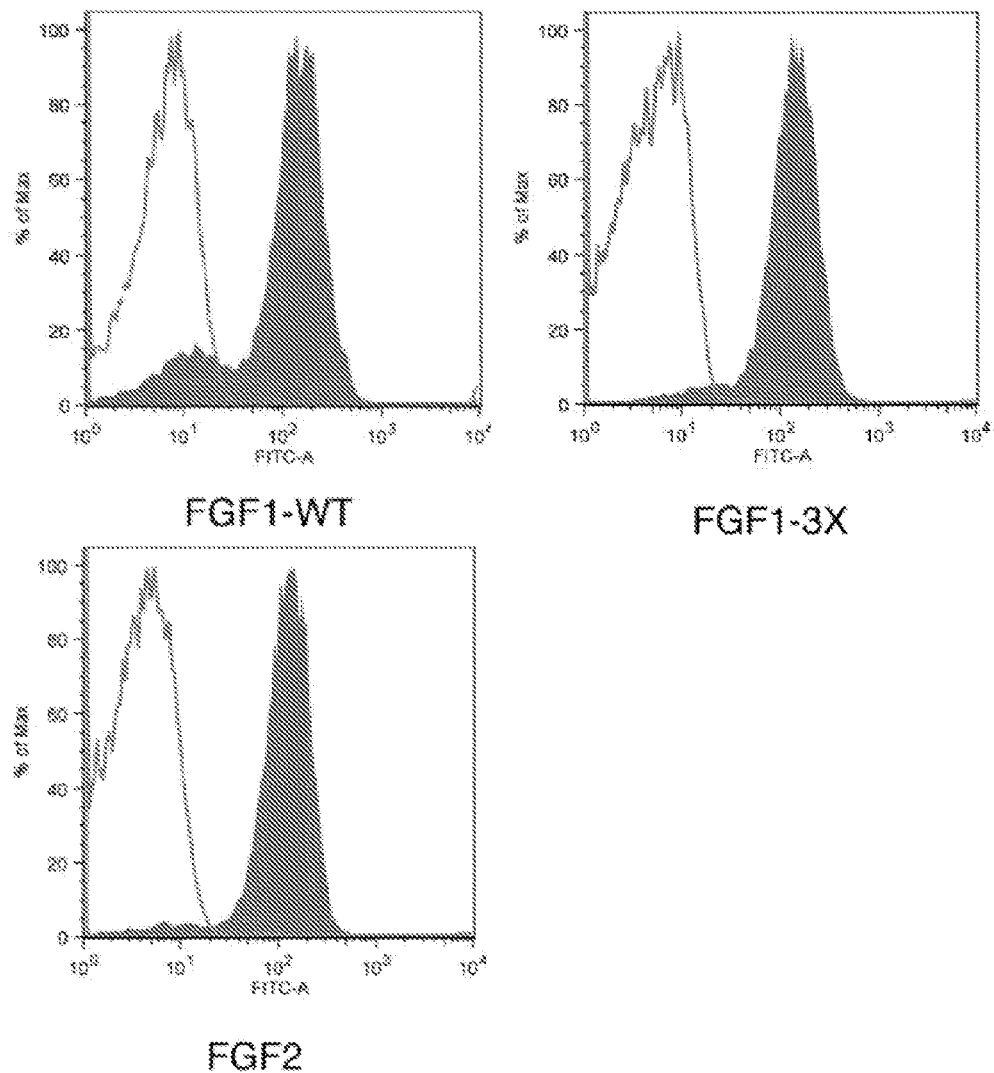
Figure 4E:

Mutated FGF-1 induced ERK phosphorylation similar to the wild type protein (FIG. 4C). In contrast to wild type FGF-1, FGF-1 having the Q40P, S47I, H93G, and/or K112N mutation was able to maintain ERK phosphorylation after 24 hours (FIG. 3C). Heparin further increased thermostability of FGF-1 3X (Q40P, S47I, and H93G) and FGF-2, while the stability of FGF-1 4X (Q40P, S47I, H93G, and K112N) was not further enhanced by heparin (FIG. 3D). The 3X and 4X mutated FGF-1 proteins increased ES cell growth and pluripotency (FIGS. 3E and 3F and 4D). Human ES cells maintained in media with FGF-1 3X and FGF-1 4X for 2 months had normal karyotypes and gene expression characteristic of human pluripotent cells (FIG. 4D). Truncation of FGF-1 does not impact thermostability of the protein (FIG. 4E).

Example 3

FGF Stability Affects Differentiation of Human Pluripotent Stem Cells

Figure 5A:
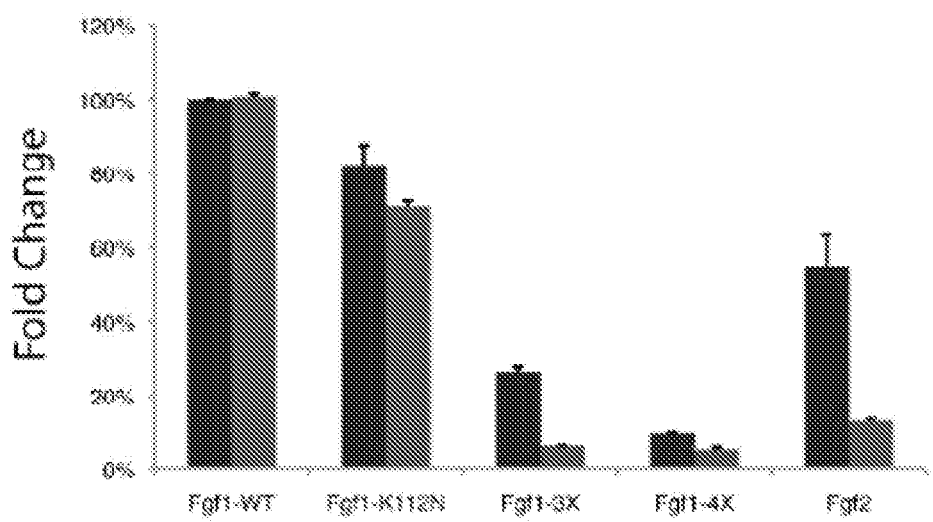
FIGS. 5A and 5B show that human ES cells differentiate in the absence of TGFβ. H1 cells were maintained in E8 media with different FGFs, and GATA2 and HAND1 were detected by RT-qPCR. GAPDH was used as control, and expression level was normalized with the expression in FGF-1-WT. Blue columns (left column in each pair) represent expression without heparin, and red columns (right column in each pair) are for the expression with heparin.
Figure 5B:
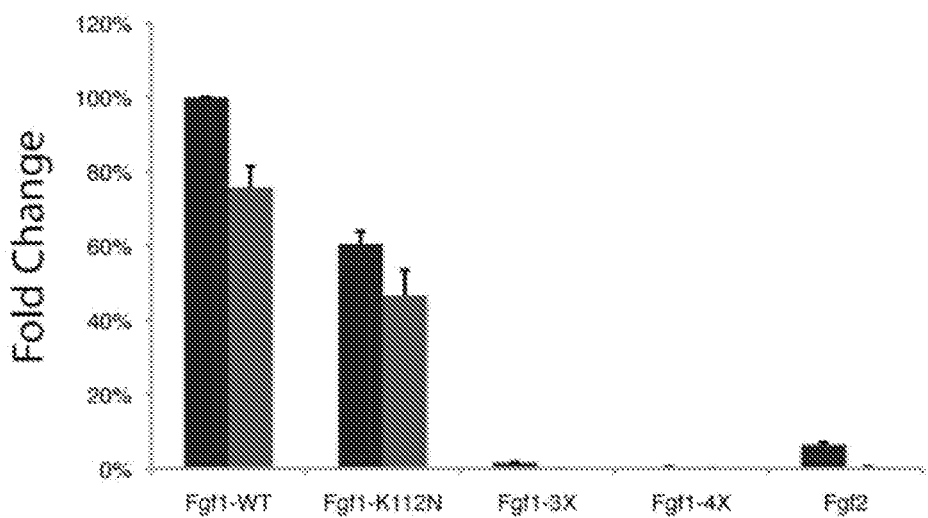

ES cells grown in culture in the absence of TGF-β express genes indicative of differentiation, such as GATA2 and HAND1. FGF-2 was sufficient to temporarily suppress the expression of specific differentiation marker genes, and heparin significantly enhanced this function of FGF-1 3X and FGF-2 (FIGS. 5A and 5B) demonstrating that thermostability influences the specific quality of FGF function.

Figure 5C:
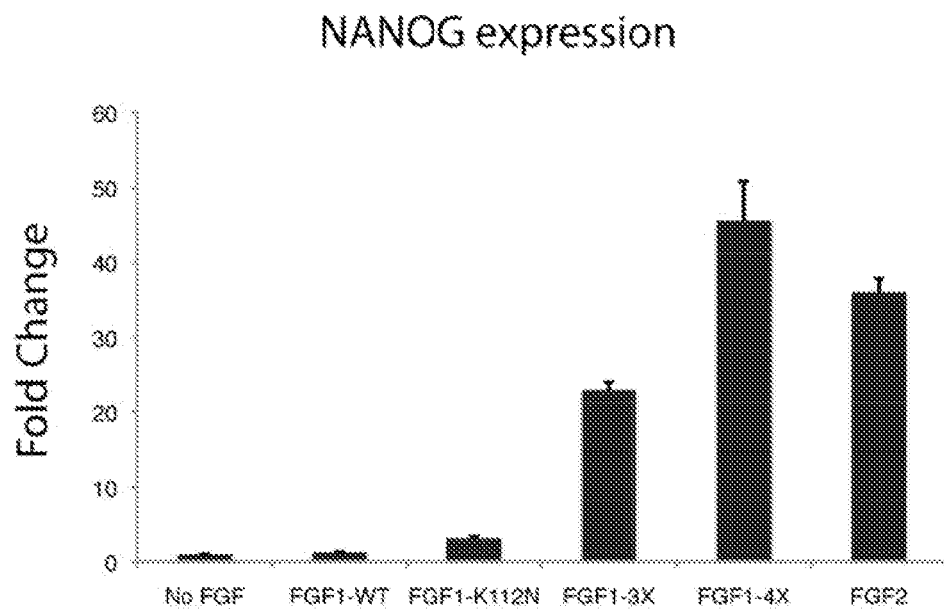
FIGS. 5C and 5D show that FGF and BMP4 induce mesodermal specific differentiation in human ES cells. Cells were incubated with BMP4 and different FGFs for 48 hours, and the expression of NANOG and T were detected by RT-qPCR.
Figure 5D:
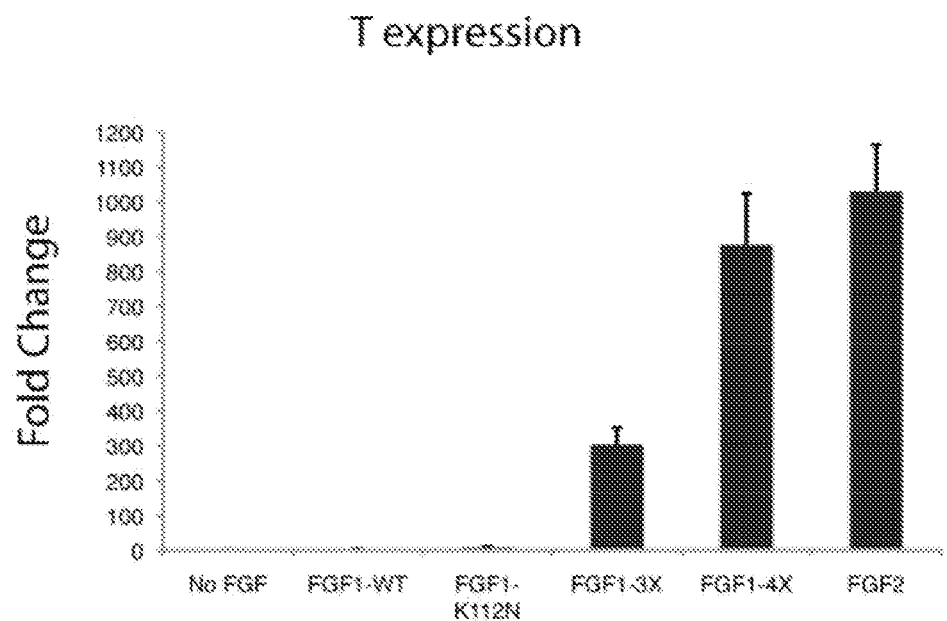

To determine if FGF stability affects its ability to support mesodermal differentiation, FGF-1 K112N, 3X and 4X mutants were added to ES cells and expression of the mesodermal marker Brachyury (T) and NANOG, which is associated with Brachyury (T) expression, was analyzed. Human ES cells differentiated into mesodermal lineage cells in the presence of BMP4, as evidenced by their upregulated expression of Brachyury (T) and NANOG. Cells treated with thermostable FGF-1 also expressed significantly higher levels of NANOG (FIG. 5B) and Brachyury (T) (FIG. 5C).

Example 4

Figure 6:
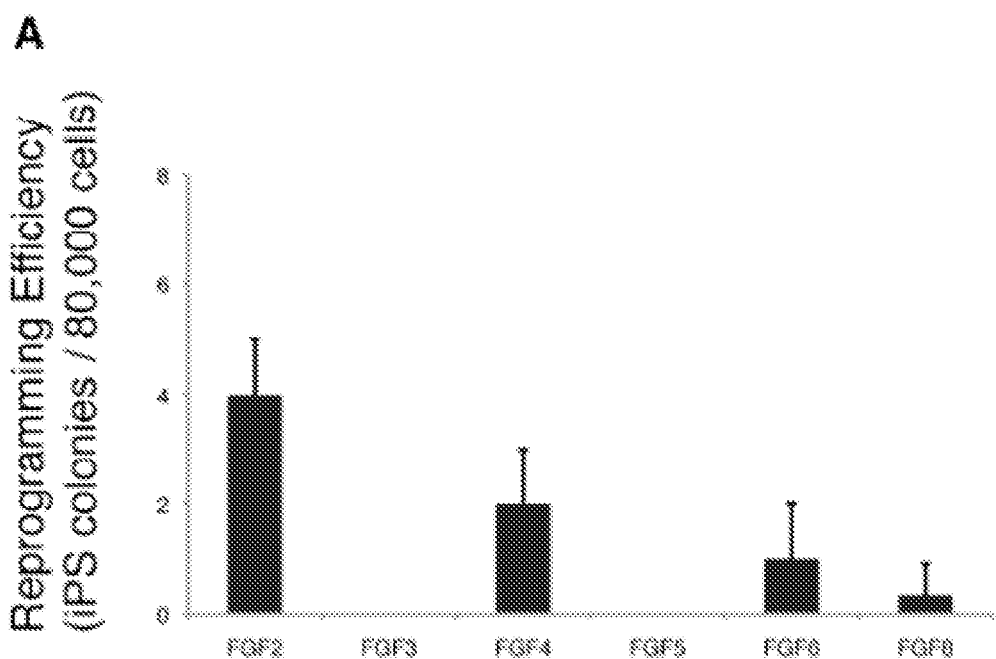
FIG. 6 illustrates that specific FGFs affect reprogramming efficiency in fibroblasts. Foreskin fibroblasts were reprogrammed with viral-free approach (e.g., U.S. Patent Application Publication No. 2010/0184227). Different FGFs (100 ng/ml) were used to replace FGF-2 in culture media at each reprogramming stage. iPS colonies were scored 30 days after the transfection of reprogramming factors.

FGF Stability Affects Reprogramming of Somatic Cells to Human Pluripotent Stem Cells Methods To determine if FGF thermostability affects reprogramming, foreskin fibroblasts were reprogrammed using a viral-free approach as previously described (Chen et al., 2011). Different FGFs (100 ng/ml) were used to replace FGF-2 in culture media at each reprogramming stage. iPS colonies were scored 30 days after the transfection of reprogramming factors (FIG. 6).

iPS Cell Derivation in Defined Conditions.

Briefly, plasmid combinations #19 (pEP4-E-O2S-E-T2K, pEP4-E-O2S-E-N2K and pCEP4M2L) were used for reprogramming unless mentioned otherwise. Plasmids and EBNA mRNA were electroporated into fibroblast cells on Amaxa apparatus according to company instructions. One million cells were used in each electroporation, which were then plated into two 6-well plates. E8+hydrocortisone media were used for the first 5-10 days after electroporation. When confluency reached ~20%, hydrocortisone was removed. ES-like iPS cell colonies appeared after ~25 days. Cells were then picked into individual wells containing E8 medium with TGF-beta.

Results

Figure 5E:
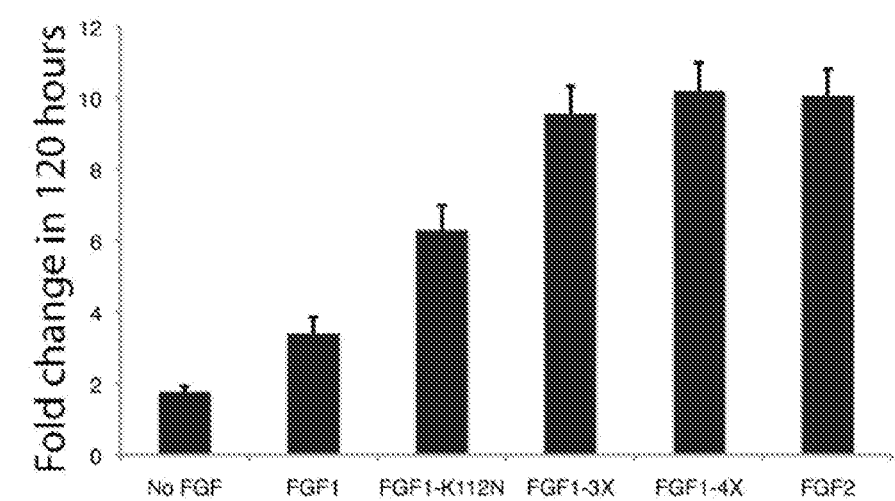
FIG. 5E depicts human fibroblast cells maintained in defined fibroblast media with different FGFs; cells were counted after 120 hours.
Figure 5F:
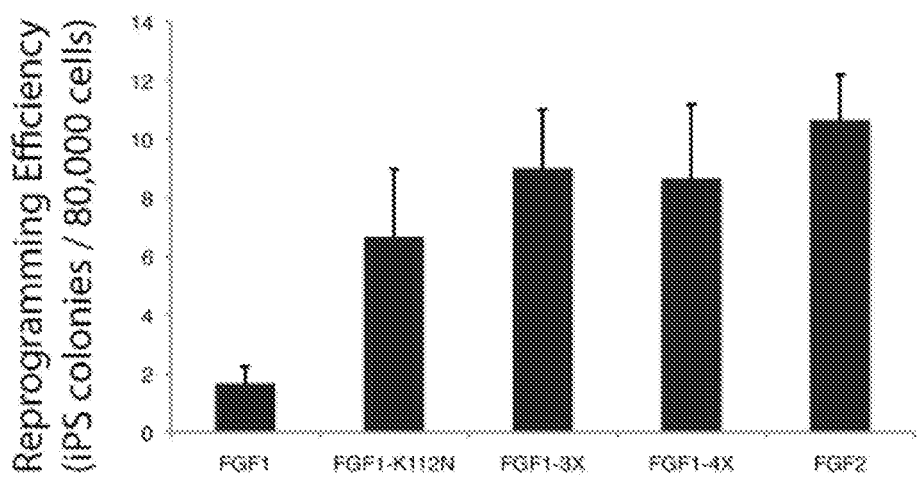
FIG. 5F depicts human fibroblast cells reprogrammed in defined conditions with episomal vectors with different FGFs. iPS cells were scored after 25 days.

Thermostable FGF-1 significantly improves cell growth of human fibroblasts (FIG. 5E). Thermostable FGF-1 also significantly improved reprogramming efficiency relative to truncated wild type FGF-1 (FIG. 5F and FIG. 6).

SEQUENCES

SEQ ID NO: 1: nucleic acid sequence of truncated wild type human FGF-1
ATGGCTAATTACAAGAAGCCCAAACTCCTCTACTGTAGCAACGGGGGCCACTTCC
TGAGGATCCTTCCGGATGGCACAGTGGATGGGACAAGGGACAGGAGCGACCAGC
ACATTCAGCTGCAGCTCAGTGCGGAAAGCGTGGGGGAGGTGTATATAAAGAGTA
CCGAGACTGGCCAGTACTTGGCCATGGACACCGACGGGCTTTTATACGGCTCACA
GACACCAAATGAGGAATGTTTGTTCCTGGAAAGGCTGGAGGAGAACCATTACAA
CACCTATATATCCAAGAAGCATGCAGAGAAGAATTGGTTTGTTGGCCTCAAGAA
GAATGGGAGCTGCAAACGCGGTCCTCGGACTCACTATGGCCAGAAAGCAATCTT
GTTTCTCCCCCTGCCAGTCTCTTCTGATTAA SEQ ID NO: 2: amino acid sequence of truncated wild type human FGF-1 (bold,
underlined residues are Q40, S47, H93, and K112)
MANYKKPKLLYCSNGGHFLRILPDGTVDGTRDRSDQHIQLQLSAESVGEVYIKSTET
GQYLAMDTDGLLYGSQTPNEECLFLERLEENHYNTYISKKHAEKNWFVGLKKNGSC
KRGPRTHYGQKAILFLPLPVSSD SEQ ID NO: 3 amino acid sequence of truncated wild type human FGF-1 (SEQ ID NO: 2)
with Q40P, S47I, and H93G substitutions
MANYKKPKLLYCSNGGHFLRILPDGTVDGTRDRSDPHIQLQLIAESVGEVYIKSTETG
QYLAMDTDGLLYGSQTPNEECLFLERLEENGYNTYISKKHAEKNWFVGLKKNGSCK
RGPRTHYGQKAILFLPLPVSSD SEQ ID NO: 4 amino acid sequence of truncated wild type human FGF-1 (SEQ ID NO: 2)
with Q40P, S47I, H93G, and K112N substitutions
MANYKKPKLLYCSNGGHFLRILPDGTVDGTRDRSDQHIQLQLSAESVGEVYIKSTET
GQYLAMDTDGLLYGSQTPNEECLFLERLEENHYNTYISKKHAEKNWFVGLNKNGSC
KRGPRTHYGQKAILFLPLPVSSD The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method for culturing human pluripotent stem cells, comprising the step of culturing a human pluripotent stem cell in a fully defined culture medium comprising factors that support pluripotency of human pluripotent stem cells, wherein the culture medium comprises an FGF comprising the amino acid sequence of SEQ ID NO:3 or SEQ ID NO:4.

2. The method of claim 1, wherein the human pluripotent stem cells are selected from the group consisting of human embryonic stem cells and human induced pluripotent stem cells.

3. The method of claim 1, wherein the medium further comprises heparin.

4. The method of claim 1, wherein the FGF is provided in the culture medium at a concentration of less than 40 ng/ml.

5. The method of claim 1, wherein the FGF comprises the amino acid sequence of SEQ ID NO:3.

6. The method of claim 5, wherein the amino acid sequence of the FGF consists of the amino acid sequence of SEQ ID NO:3.

7. The method of claim 1, wherein the FGF comprises the amino acid sequence of SEQ ID NO:4.

8. The method of claim 7, wherein the amino acid sequence of the FGF consists of the amino acid sequence of SEQ ID NO:4.

9. A fully-defined culture medium comprising:
(i) an FGF comprising the amino acid sequence of SEQ ID NO:3 or SEQ ID NO:4;
(ii) insulin or an insulin-like growth factor (IGF); and
(iii) TGFβ or Nodal;
wherein the culture medium supports culture of human pluripotent stem cells in an undifferentiated state.

10. The medium of claim 9, wherein the FGF comprises the amino acid sequence of SEQ ID NO:3.

11. The medium of claim 10, wherein the amino acid sequence of the FGF consists of the amino acid sequence of SEQ ID NO:3.

12. The medium of claim 10, wherein the FGF comprises the amino acid sequence of SEQ ID NO:4.

13. The medium of claim 12, wherein the amino acid sequence of the FGF consists of the amino acid sequence of SEQ ID NO:4.

14. The medium of claim 9, wherein the FGF is provided in the medium at a concentration of less than 40 ng/ml.

15. A composition comprising:
a human pluripotent stem cell and a fully defined culture medium comprising
(i) an FGF comprising the amino acid sequence of SEQ ID NO:3 or SEQ ID NO:4;
(ii) insulin or an IGF; and
(iii) TGFβ or Nodal; and
wherein the fully defined culture medium maintains the human pluripotent cell in an undifferentiated state.

16. The composition of claim 15, wherein the FGF comprises the amino acid sequence of SEQ ID NO:3.

17. The composition of claim 16, wherein the FGF comprises the amino acid sequence of SEQ ID NO:4.

18. The composition of claim 15, wherein the FGF is provided in the medium at a concentration of less than 40 ng/ml.

19. The composition of claim 15, wherein the amino acid sequence of the FGF consists of the amino acid sequence of SEQ ID NO:3.

20. The composition of claim 15, wherein the amino acid sequence of the FGF consists of the amino acid sequence of SEQ ID NO:4.

21. The method of claim 1, wherein the culture medium is albumin-free.

22. The composition of claim 9, wherein the culture medium is albumin-free.

23. The composition of claim 15, wherein the culture medium is albumin-free.

* * * * *

UNITED STATES PATENT AND TRADEMARK OFFICE
CERTIFICATE OF CORRECTION

PATENT NO. : 9,023,644 B2  
APPLICATION NO. : 13/717055  
DATED : May 5, 2015  
INVENTOR(S) : Guokai Chen and James A. Thomson Page 1 of 1

It is certified that error appears in the above-identified patent and that said Letters Patent is hereby corrected as shown below:

In the Specification

Column 13, line 37 - "µA" should read "µl"

Column 13, line 46 - "500" should read "5000"

Signed and Sealed this
Twenty-ninth Day of September, 2015

Michelle K. Lee
*Director of the United States Patent and Trademark Office*